(12) United States Patent
Thompson et al.

(10) Patent No.: US 6,623,518 B2
(45) Date of Patent: Sep. 23, 2003

(54) IMPLANT DELIVERY SYSTEM WITH INTERLOCK

(75) Inventors: Paul J. Thompson, New Hope, MN (US); Nathan T. Lee, Golden Valley, MN (US)

(73) Assignee: ev3 Peripheral, Inc., Plymouth, MN (US)

( * ) Notice: Subject to any disclaimer, the term of this patent is extended or adjusted under 35 U.S.C. 154(b) by 0 days.

(21) Appl. No.: 09/795,047

(22) Filed: Feb. 26, 2001

(65) Prior Publication Data

US 2002/0120322 A1 Aug. 29, 2002

(51) Int. Cl.$^7$ .............................. A61F 2/06; A61F 11/00
(52) U.S. Cl. ...................................... 623/1.11; 606/108
(58) Field of Search ........................ 623/1.11; 606/108, 606/192, 194

(56) References Cited

U.S. PATENT DOCUMENTS

| | | | |
|---|---|---|---|
| 4,768,507 A | 9/1988 | Fischell et al. | |
| 4,913,141 A | 4/1990 | Hillstead | |
| 5,026,377 A | 6/1991 | Burton et al. | |
| 5,480,423 A | 1/1996 | Ravenscroft et al. | |
| 5,484,444 A | 1/1996 | Braunschweiler et al. | |
| 5,591,172 A | 1/1997 | Bachmann et al. | |
| D380,266 S | * 6/1997 | Boatman et al. ............ | D24/155 |
| D380,831 S | * 7/1997 | Kavteladze et al. ....... | D24/155 |
| 5,695,499 A | 12/1997 | Helgerson et al. | |
| 5,759,186 A | 6/1998 | Bachmann et al. | |
| 5,817,102 A | * 10/1998 | Johnson et al. ............. | 606/108 |
| 5,954,729 A | 9/1999 | Bachmann et al. | |
| 6,004,328 A | 12/1999 | Solar | |
| 6,077,295 A | 6/2000 | Limon et al. | |
| 6,077,297 A | * 6/2000 | Robinson et al. .......... | 623/1.11 |
| 6,120,522 A | 9/2000 | Vrba et al. | |
| 6,132,460 A | 10/2000 | Thompson | |
| 6,132,461 A | 10/2000 | Thompson | |
| 6,214,036 B1 | 4/2001 | Letendre et al. | |
| 6,267,783 B1 | * 7/2001 | Letendre et al. ........... | 623/1.13 |
| 6,293,966 B1 | * 9/2001 | Frantzen .................... | 623/1.15 |
| 6,315,790 B1 | 11/2001 | Gerberding et al. | |

FOREIGN PATENT DOCUMENTS

| | | |
|---|---|---|
| EP | 0 709 068 A2 | 5/1996 |
| EP | 0 775 470 A1 | 5/1997 |
| EP | 0 943 302 A2 | 9/1999 |
| EP | 0 947 179 A2 | 10/1999 |
| EP | 0 947 179 A3 | 12/1999 |
| EP | 1 000 590 A1 | 5/2000 |
| EP | 1 086 665 A1 | 3/2001 |
| EP | 1 157 673 A2 | 11/2001 |
| EP | 1 212 989 A2 | 6/2002 |

OTHER PUBLICATIONS

Brochure entitled "memotherm FLEXX Vascular Stent" by Angiomed GmbH & Co. Medizintechnik KG, (Sep. 1999).

\* cited by examiner

*Primary Examiner*—Corrine McDermott
*Assistant Examiner*—Alvin Stewart
(74) *Attorney, Agent, or Firm*—Merchant & Gould P.C.

(57) ABSTRACT

An implant delivery system includes outer and inner elongated, flexible tubular members each having a distal and proximal end. The outer tubular member is sized to be passed through the body lumen with the distal end advanced to the deployment site and with the proximal end remaining external of the patient's body for manipulation by an operator. The inner tubular member is sized to be received within the outer tubular member. The outer tubular and inner tubular members are axially slidable relative to one another between a transport position and the deploy position. The inner tubular member has an implant attachment location at its distal end. The implant attachment location is covered by the outer tubular member when the inner and outer tubular members are in the transport position. The implant attachment location is exposed when the inner and outer tubular members are in the deploy position. Sliding relative motion between the inner and outer members exposes first a distal end of the implant attachment location and last a proximal end of the stent attachment location. An implant is carried at the implant attachment location. A proximal end of the implant is interlocked with the inner member to be restricted from axial movement relative thereto until the distal end of said outer tubular member moves proximally to the proximal end of the implant attachment location.

42 Claims, 13 Drawing Sheets

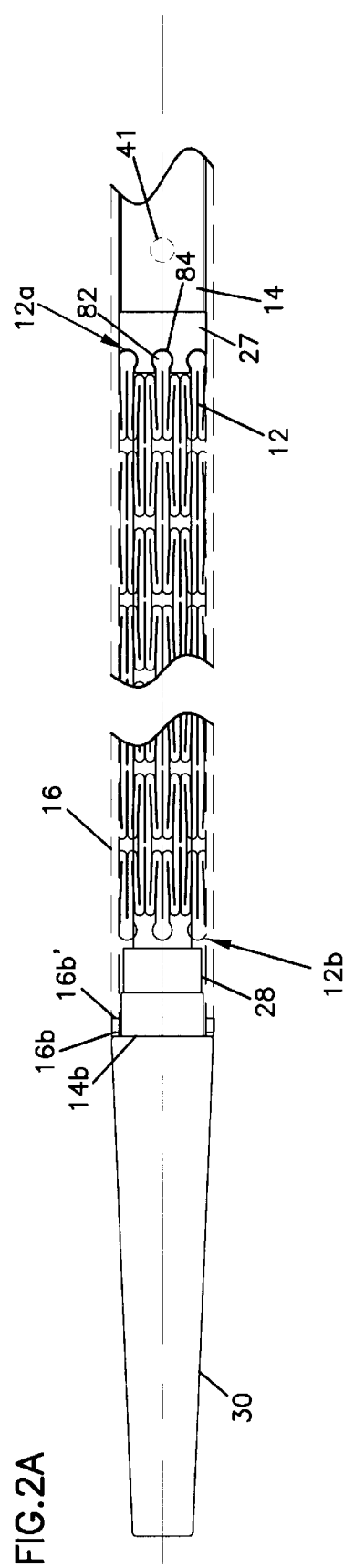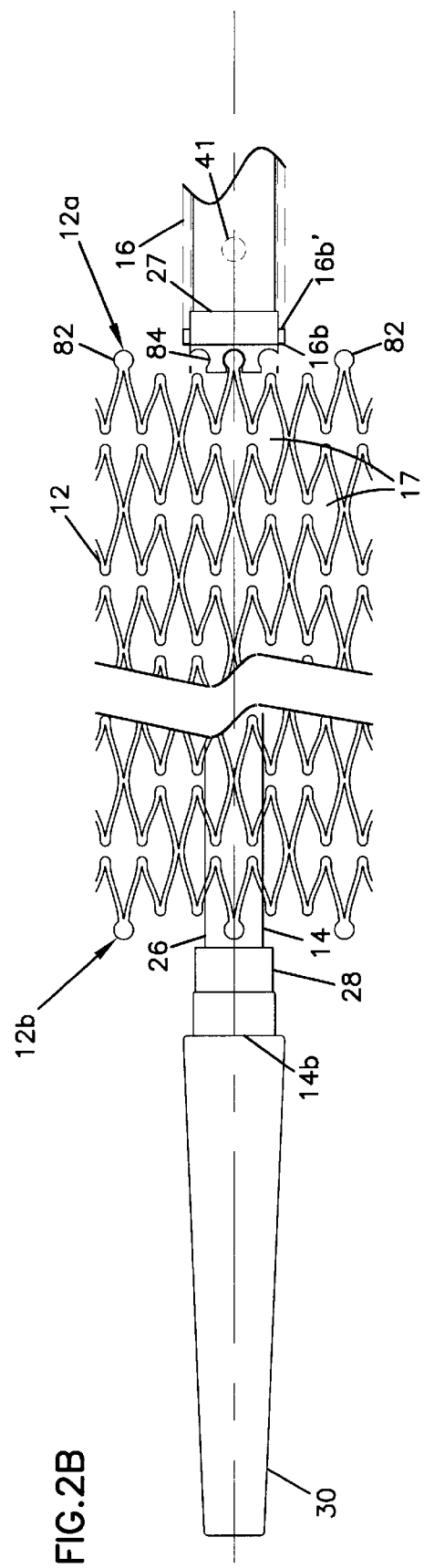
FIG.2A
FIG.2B

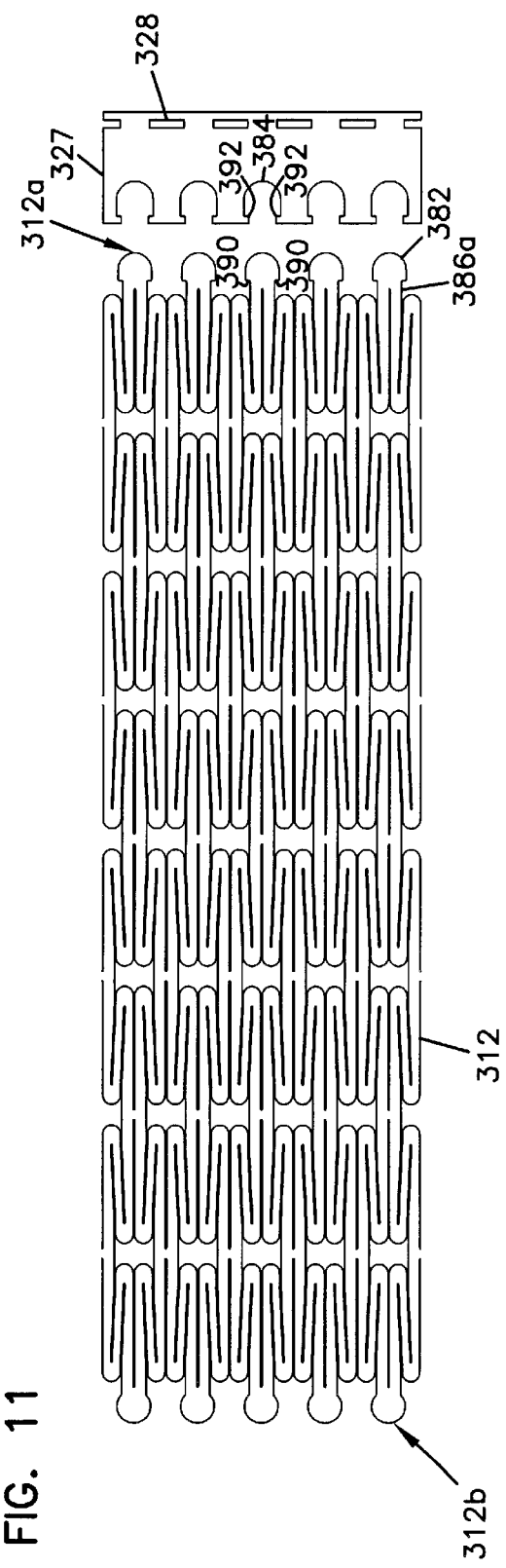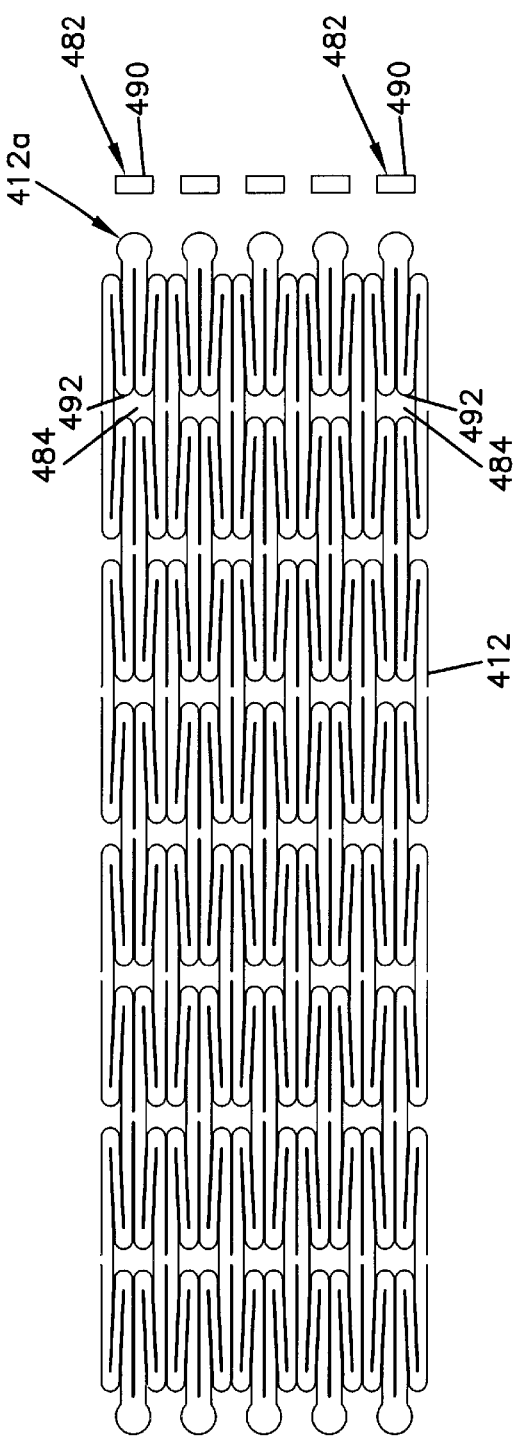

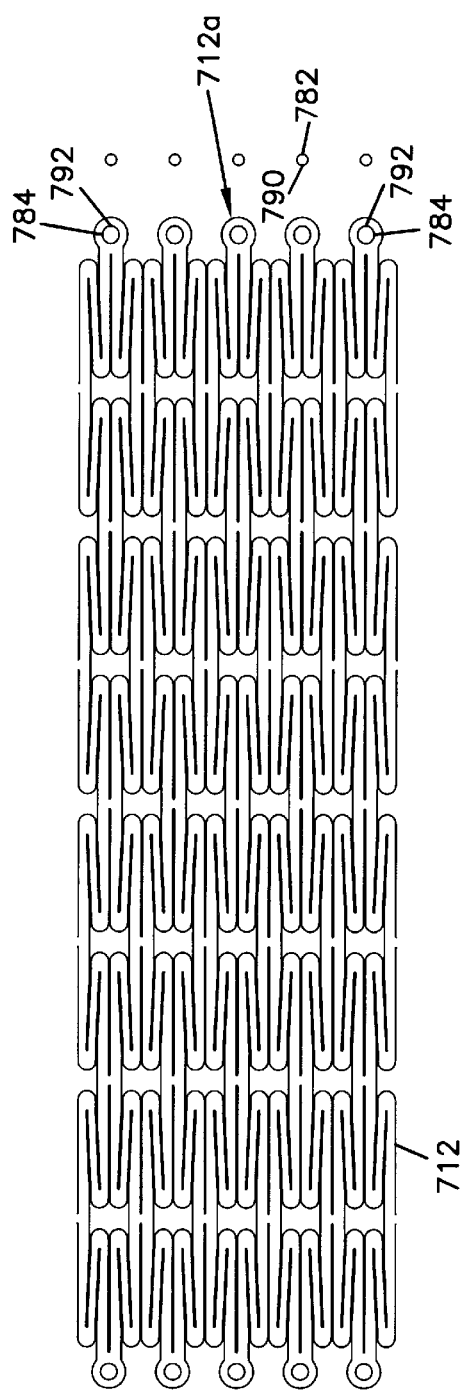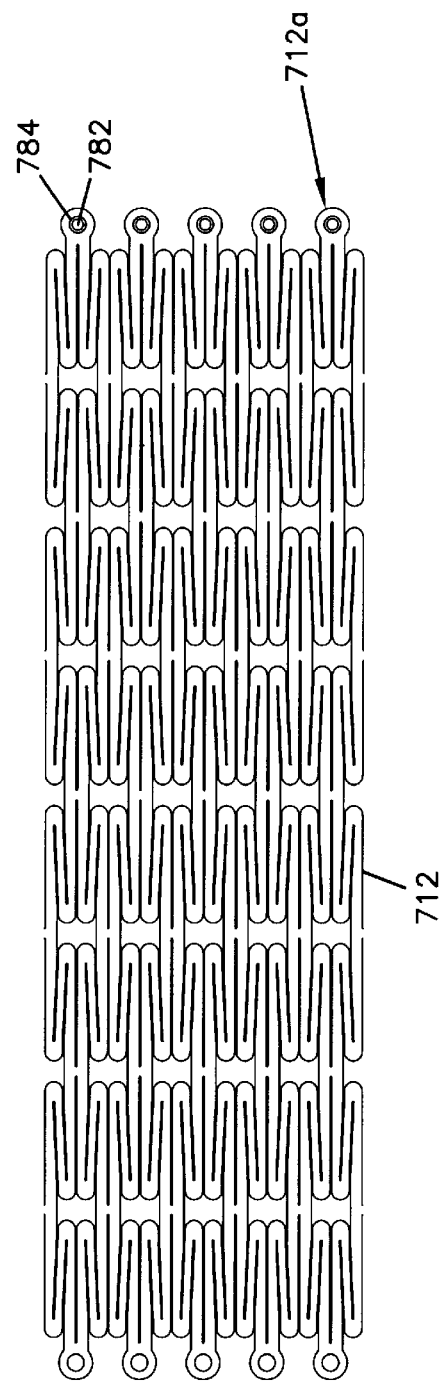
FIG. 15A
FIG. 15B

IMPLANT DELIVERY SYSTEM WITH INTERLOCK

BACKGROUND OF THE INVENTION

1. Field of Invention

This invention pertains to a system for delivering an implant to a site in a body lumen. More particularly, this invention pertains to a delivery system for a self-expandable implant such as a stent.

2. Description of the Prior Art

Stents are widely used for supporting a lumen structure in a patient's body. For example, stents may be used to maintain patency of a coronary artery, other blood vessel or other body lumen.

Commonly, stents are commonly metal, tubular structures. Stents are passed through the body lumen in a collapsed state. At the point of an obstruction or other deployment site in the body lumen, the stent is expanded to an expanded diameter to support the lumen at the deployment site.

In certain designs, stents are open-celled tubes which are expanded by inflatable balloons at the deployment site. Other stents are so-called "self-expanding" stents. Self-expanding stents do not use balloons or other application of force to a collapsed stent to cause the expansion of the stent. An example of a self-expanding stent is a coil structure which is secured to a stent delivery device under tension in a collapsed state. At the deployment site, the coil is released so that the coil can expand to its enlarged diameter. Other self-expanding stents are made of so-called shape-memory metals such as nitinol. Such shape-memory stents experience a phase change at the elevated temperature of the human body. The phase change results in expansion from a collapsed state to an enlarged state.

A delivery technique for shape-memory alloy stents is to mount the collapsed stent on a distal end of a stent delivery system. Such a system would include an outer tubular member and an inner tubular member. The inner and outer tubular members are axially slideable relative to one another. The stent (in the collapsed state) is mounted surrounding the inner tubular member at its distal end. The outer tubular member (also called the outer sheath) surrounds the stent at the distal end.

Prior to advancing the stent delivery system through the body lumen, a guide wire is first passed through the body lumen to the deployment site. The inner tube of the delivery system is hollow throughout its length such that it can be advanced over the guide wire to the deployment site.

The combined structure (i.e., stent mounted on stent delivery system) is passed through the patient's lumen until the distal end of the delivery system arrives at the deployment site within the body lumen. The deployment system may include radio-opaque markers to permit a physician to visualize positioning of the stent under fluoroscopy prior to deployment.

At the deployment site, the outer sheath is retracted to expose the stent. The exposed stent is now free to expand within the body lumen. Following expansion of the stent, the inner tube is free to pass through the stent such that the delivery system can be removed through the body lumen leaving the stent in place at the deployment site.

In prior art devices, the stent may prematurely deploy as the outer tube is retracted. Namely, with the outer tube partially retracted, the exposed portion of the stent may expand resulting in the remainder of the stent being squeezed out of the outer tube. This can result in the stent being propelled distally beyond a desired deployment site. Also, once the stent partially unsheathed, it is sometimes determined that the stent placement needs to be adjusted. With existing systems, this is difficult since the stent has a tendency to force itself out of the sheath thereby making adjustments difficult. What is needed is a system that retains the stent on the catheter even when a majority of the stent has been exposed by retraction of the sheath. What is also needed is a system that allows a stent to be re-sheathed even after a majority of the stent has been exposed by retraction of the sheath.

It is an object of the present invention to provide improved structures for self-expandable implant delivery systems such as stent delivery systems.

SUMMARY OF THE INVENTION

One aspect of the present invention relates to a method for deploying a self-expandable implant with a deployment system. The deployment system includes a sheath for holding the implant in a compressed orientation. The implant includes an implant body that extends along an axis between first and second ends. The implant also includes an interlock surface that faces in an axial direction. The interlock surface is preferably located within 5 millimeters of the first end of the implant. The method is initiated by generating relative movement between the implant and the sheath to expose the implant. As the implant is exposed, the interlock surface of the implant is engaged by a retainer to prevent the implant from prematurely exiting the sheath. After the implant has been exposed beyond the interlock surface, the interlock surface is disengaged from the retainer by self-expanding the implant. Another aspect of the present invention relates to systems for practicing the above-described method.

BRIEF DESCRIPTION OF THE DRAWINGS

FIG. 2A is an enlarged cross-sectional view of detail A of FIG. 1 with the stent in a compressed orientation;

FIG. 2B is an enlarged cross-sectional view of detail A of FIG. 1 with the stent in a deployed (i.e., expanded) orientation;

FIG. 11 is a laid flat, plan view of a sixth stent having an interlock structure that interlocks with an interlock structure of a mating collar;

FIG. 12 is a laid flat, plan view of a seventh stent having an interlock structure that interlocks with rectangular posts formed on an inner body of a catheter;

FIG. 15A is a laid flat, plan view of a tenth stent having an interlock structure that interlocks with outwardly projecting posts formed on the inner body of a catheter; and FIG. 15B shows the stent of FIG. 15A interlocked with the posts.

DETAILED DESCRIPTION

Figure 1:
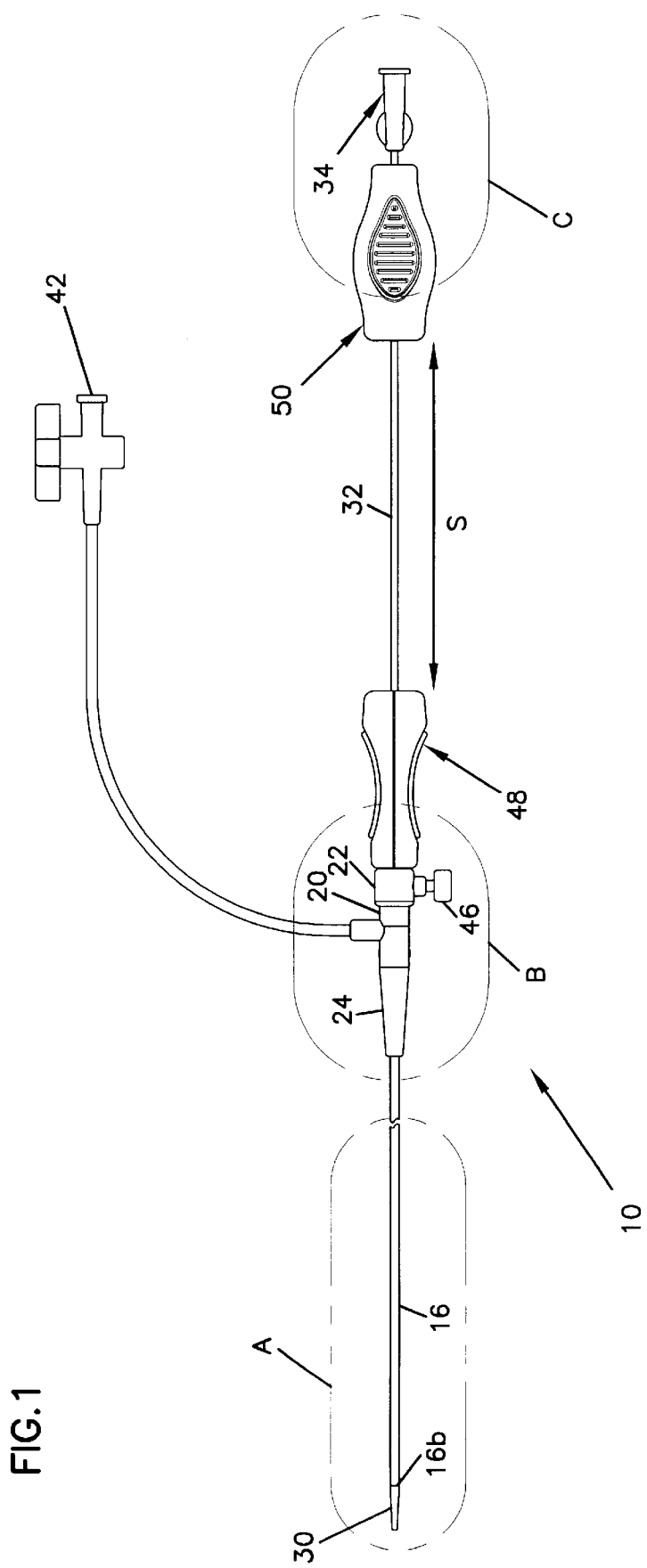
FIG. 1 is a side elevation view of a stent delivery system according to the present invention.

With reference now to the various drawing figures in which identical elements are numbered identically throughout, a description of a preferred embodiment of the present invention will now be provided.

With initial references to FIGS. 1–4, a stent delivery system 10 is shown. The stent delivery system 10 is for delivery of a stent 12 to a deployment site in a body lumen of a patient's body. By way of non-limiting, representative example, the stent 12 may be a self-expanding, open-celled, tubular stent having a construction such as that shown in U.S. Pat. No. 6,132,461 and formed of a self-expanding, shape-memory or superelastic metal such as nitinol, or the like. The stent 12 may also be a coil stent or any other self-expanding stent. The stent 12 includes a proximal end 12a and a distal end 12b. Another representative stent is shown in U.S. patent application Ser. No. 09/765,725, filed Jan. 18, 2001 and entitled STENT, which is hereby incorporated by reference.

The stent 12 is carried on the stent delivery system 10 in a collapsed (or reduced diameter) state as shown in FIG. 2A. Upon release of the stent 12 from the stent delivery system 10 (as will be described), the stent 12 expands to an enlarged diameter (see FIG. 2B) to abut against the walls of the patient's lumen in order to support patency of the lumen.

The stent delivery system 10 includes an inner tubular member 14 (i.e., also referred to as an elongated member) and an outer tubular member 16. Both of the inner and outer tubular members 14 and 16 extend from proximal ends 14a, 16a to distal ends 14b, 16b.

The outer tubular member 16 is sized to be axially advanced through the patient's body lumen. The tubular member 16 is preferably sufficiently long for the distal end 16b to be placed near the deployment site in the patient's body lumen with the proximal end 16a remaining external to the patient's body for manipulation by an operator. By way of example, the outer tubular member 16 (also referred to as a sheath) may be a braid-reinforced polyester of tubular construction to resist kinking and to transmit axial forces along the length of the sheath 16. The outer tubular member 16 may be of widely varying construction to permit varying degrees of flexibility of the outer tubular member 16 along its length.

Figure 3:
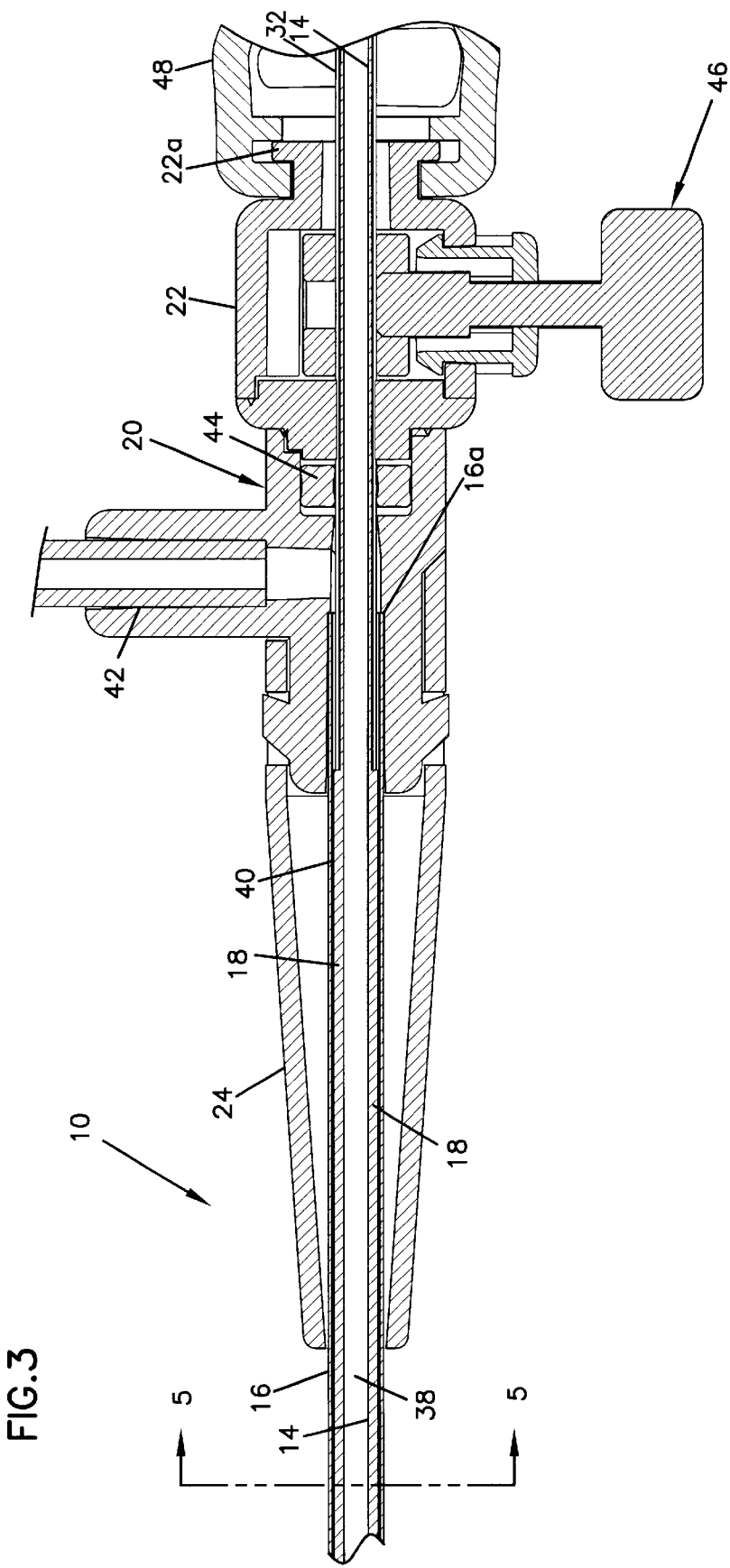
FIG. 3 is an enlarged cross-sectional view of detail B of FIG. 1.

As shown in FIG. 3, the proximal end 16a of the outer tubular member 16 is bonded to a manifold housing 20. The manifold housing 20 is threadedly connected to a lock housing 22. A strain relief jacket 24 is connected to the manifold housing 20 and surrounds the outer tubular member 16 to provide strain relief for the outer tubular member 16.

The inner tubular member 14 is preferably formed of nylon but may be constructed of any suitable material. As shown in FIG. 2B, the inner tubular member 14 defines a stent attachment location 26. The inner tubular member 14 also includes markers 27, 28 that are attached to an outer surface of the inner tubular member 14 (e.g., by techniques such as adhesive, heat fusion, interference fit or other techniques). The attachment location 26 is positioned between the markers 27, 28. The radio-opaque markers 27, 28 permit a physician to accurately determine the position of the stent attachment location 26 within the patient's lumen under fluoroscopic visualization. As will be described later in the specification, in some embodiments, at least one of the markers 27, 28 forms a collar including a geometry that interlocks with the stent 12 to prevent axial movement of the stent 12 relative to the inner tubular member during transport and deployment of the stent 12.

A tapered and flexible distal tip member 30 is secured to the distal end 14b of the inner tubular member 14. The highly flexible distal tip member 30 permits advancement of the stent deployment system 10 through the patient's lumen and minimizes trauma to the walls of the patient's lumen.

Figure 4:
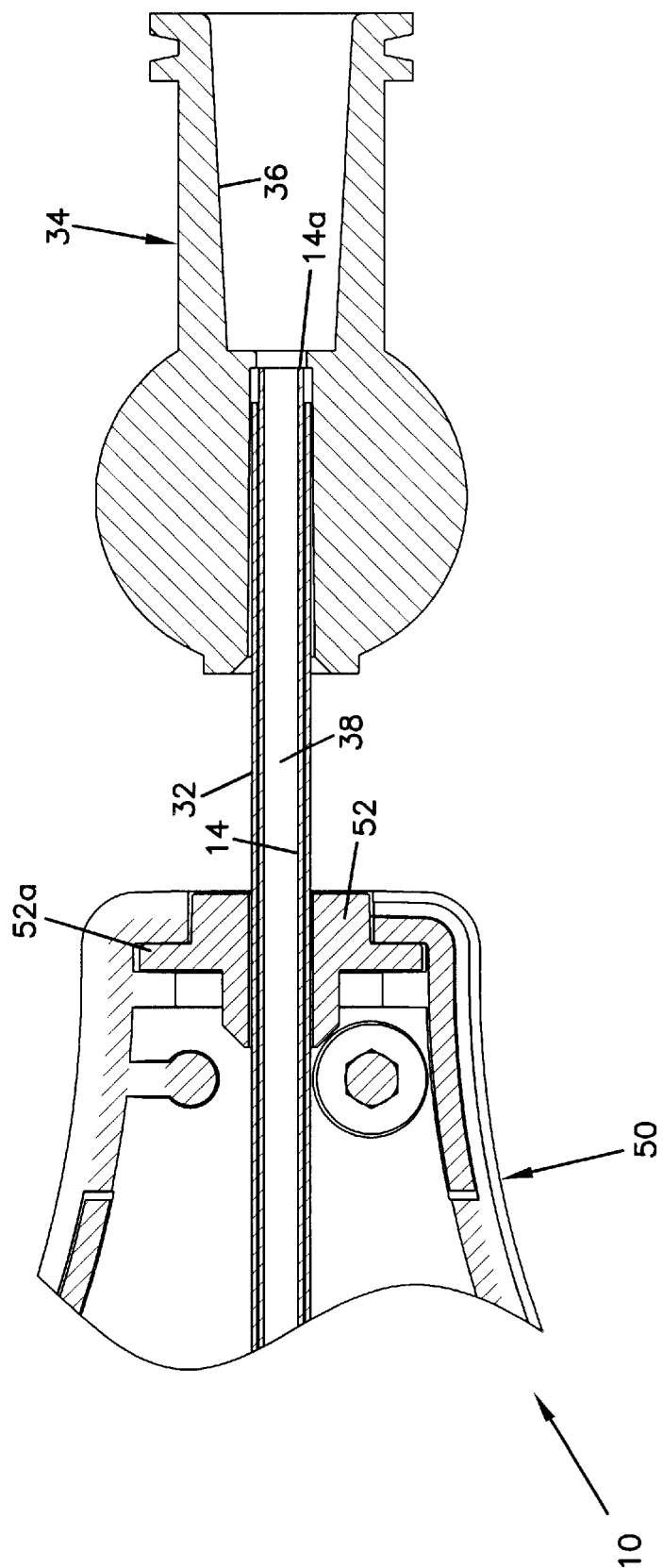
FIG. 4 is an enlarged cross-sectional view of detail C.

As best shown in FIGS. 3 and 4, the inner tube 14 passes through both the manifold housing 20 and lock housing 22. A stainless steel jacket 32 surrounds and is bonded to the inner tubular member 14.

Figure 5:
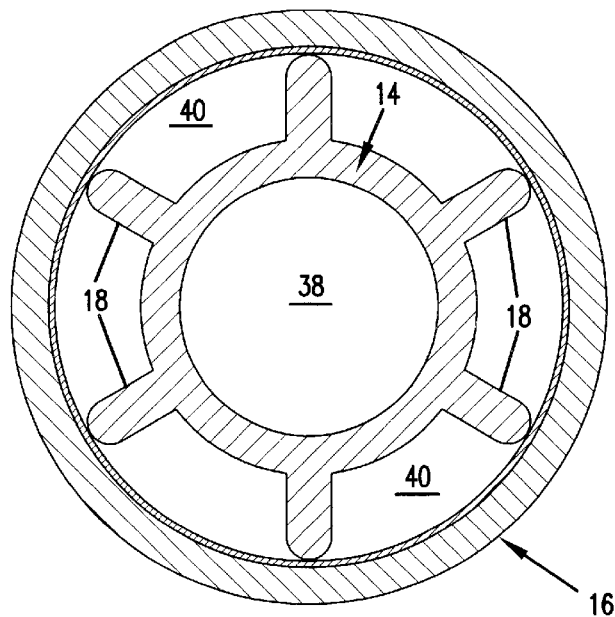
FIG. 5 is a cross-sectional view of the inner and outer tubular members of the stent delivery system of FIG. 1 taken along section line 5—5 of FIG. 3.

At the inner tube proximal end 14a, a port housing 34 is bonded to the stainless steel jacket 32. The port housing 34 has a tapered bore 36 aligned with an inner lumen 38 of the tubular member 14. The inner lumen 38 extends completely through the inner tubular member 14 so that the entire delivery system 10 can be passed over a guide wire (not shown) initially positioned within the patient's lumen. Opposing surfaces of the inner and outer tubular members 14 and 16, define a first lumen 40 (best seen in FIG. 5). As described in U.S. patent application Ser. No. 09/765,719 filed on Jan. 18, 2001 and entitled STENT DELIVERY SYSTEM WITH SPACER MEMBER, which is hereby incorporated by reference, splines 18 can be provided between the inner and outer tubular members 14 and 16.

As shown in FIG. 3, the manifold housing 20 carries an admission port 42 for injecting a contrast media into the interior of the manifold housing 20. The interior of the manifold housing 20 is in fluid flow communication with the first lumen 40. Discharge ports 41 (shown in FIGS. 2A and 2B) are formed through the outer tubular member 16 to permit contrast media to flow from the first lumen 40 into the patient's body lumen.

As shown in FIG. 3, an O-ring 44 surrounds the stainless steel jacket 32 between the manifold housing 20 and lock housing 22. Upon threaded connection of the manifold housing 20 to the lock housing 22, the O-ring 44 compresses against the stainless steel jacket 32 in sealing engagement to prevent contrast media from flowing in any path other than through the first lumen 40.

As shown in FIGS. 1 and 3, the lock housing 22 carries a threaded locking member (or lock nut) 46 which can be turned to abut the stainless steel jacket 32. The lock nut 46 can be released to free the stainless steel jacket to move axially. According, when the lock nut 46 engages the jacket 32, the jacket 32 (and attached inner tubular member 14) cannot move relative to the lock housing 22, manifold housing 20 or the outer tubular member 16. Upon release of the lock nut 46, the inner tubular member 14 and outer tubular member 16 are free to slide axially relative to one another between a transport position and a deploy position.

First and second handles 48, 50 are secured to the lock housing 22 and jacket 32, respectively. In the transport position (shown in FIG. 2A), the handles 48, 50 are spaced apart and the distal end of the outer tubular member 16 forms a sheath that covers the stent attachment location 26 to prevent premature deployment of the stent 12. When the handle 48 is pulled rearwardly toward the handle 50, the outer tubular member 16 slides rearwardly or proximally relative to the inner tubular member 14. Preferably, the outer tubular member 16 slides rearwardly a distance sufficient to fully expose the stent attachment location 26 and permit the stent 12 to freely expand toward its fully expanded diameter (see FIG. 2B). After such expansion, the stent delivery system can be proximally withdrawn through the expanded stent and removed.

As shown in FIG. 3, the first handle 48 is rotatably mounted on a flange 22a of the lock housing 22. The first handle 48 surrounds the stainless steel jacket 32 and is freely rotatable about the longitudinal axis of the jacket 32 and freely rotatable about the flange 22a. The first handle 48 is axially affixed to the lock housing 22 such that axial forces applied to the first handle 48 are transmitted through the lock housing 22 and manifold housing 20 to the outer tubular member 16 to axially move the outer tubular 16. However, rotary action of the first handle 48 about the axis of the stainless steel jacket 32 is not transmitted to the housings 20, 22 or to the outer tubular member 16 by reason of the free rotation of the first handle 48 on flange 22a.

As shown in FIG. 4, the second handle 50 is mounted on an anchor 52 that is bonded to the stainless steel jacket 32 through any suitable means (such as by use of adhesives). The anchor 52 includes a flange 52a that is radial to the axis of the stainless steel jacket 32. The second handle 50 is mounted on the flange 52a and is free to rotate on the anchor 52 about the axis of the stainless steel jacket 32. However, axial forces applied to the handle 50 are transmitted to the stainless steel jacket 32 which, being bonded to the inner tubular member 14, results in axial movement of the inner tubular member 14.

With the handle construction described above, relative axial movement between the handles 48, 50 results in relative axial movement between the inner and outer tubular members 14, 16. Rotational movement of either of the handles 48, 50 does not affect rotational positioning of the inner or outer tubular members 14, 16 and does not affect axial positioning of the inner and outer tubes 14, 16.

The free rotation of the handles 48, 50 results in ease of use for a physician who may position his or her hands as desired without fear of interfering with any axial positioning of the inner and outer tubular members 14, 16. The spacing between the handles 48, 50 is equal to the stroke between the transport position and the deploy position of the tubular members 14, 16. As a result, the spacing permits the operator to have ready visual indication of the relative axial positioning between the inner and outer tubular members 14, 16. This relative axial positioning can be fixed by engaging the lock nut 46. In any such positioning, contrast media can be injected through the admission port 42 into the chamber 40 with the contrast media flowing out of the side ports 41 into the body lumen to permit visualization under fluoroscopy.

With stent deployment systems having premounted stents of various axial lengths, the positioning of the second handle 50 on the stainless steel jacket 32 can be selected at time of assembly so that a spacing S (see FIG. 1) between the handles 48, 50 corresponds to the length of the stent 12 carried on the stent deployment system. For example, in a preferred embodiment, the spacing S is about 10 millimeters longer than the deployed length of the stent. Accordingly, the user will know that the outer tubular member 16 has been fully retracted when the handles 48, 50 have been pushed completely together to completely release the stent 12. Also, the freely rotatable handles 48, 50 are easy to hold from any angle without slippage. The lock nut 46 ensures that the stent 12 will not deploy prematurely.

A concern with existing delivery systems for self-expanding stents is control of stent delivery. For example, due to their elastic characteristics, self-expanding stents have a tendency to propel themselves axially outwardly from their restraining sheaths before the sheaths have been completely retracted. When this occurs, control of stent placement is compromised since the stent may overshoot the desired deployment site. Further, once the stent has been completely deployed, subsequent adjustment of the stent deployment location can be difficult because re-sheathing typically cannot be readily accomplished.

To address the above concerns, the delivery system 10 is preferably equipped with an interlock configuration that constrains relative axial movement between the stent 12 and the inner tube 14 until after the sheath 16 has been fully retracted. For example, when the stent 12 is mounted on the inner tube 14 and restrained in the compressed orientation by the sheath 16 as shown in FIG. 2A, a first interlock geometry (e.g., male interlock structures 82 as shown in FIG. 2A) located at the proximal end of the stent 12 interlocks with a second interlock geometry (e.g., female interlock structures 84 as shown in FIG. 2A) defined by the proximal marker 27 (also referred to as a collar). The interlock geometries remain interlocked to constrain axial movement of the stent 12 until after the sheath has been retracted beyond a predetermined location (e.g., the proximal-most end 12a of the stent 12). When the sheath 12 has been retracted beyond the predetermined location, the interlock geometry of the stent 12 is allowed to expand. As the interlock geometry of the stent expands, the interlock geometry of the stent disengages from the interlock geometry of the marker 27 thereby allowing the inner tube 14 of the catheter to be moved axially relative to the stent without interference from the interlock geometries.

Figure 6C:
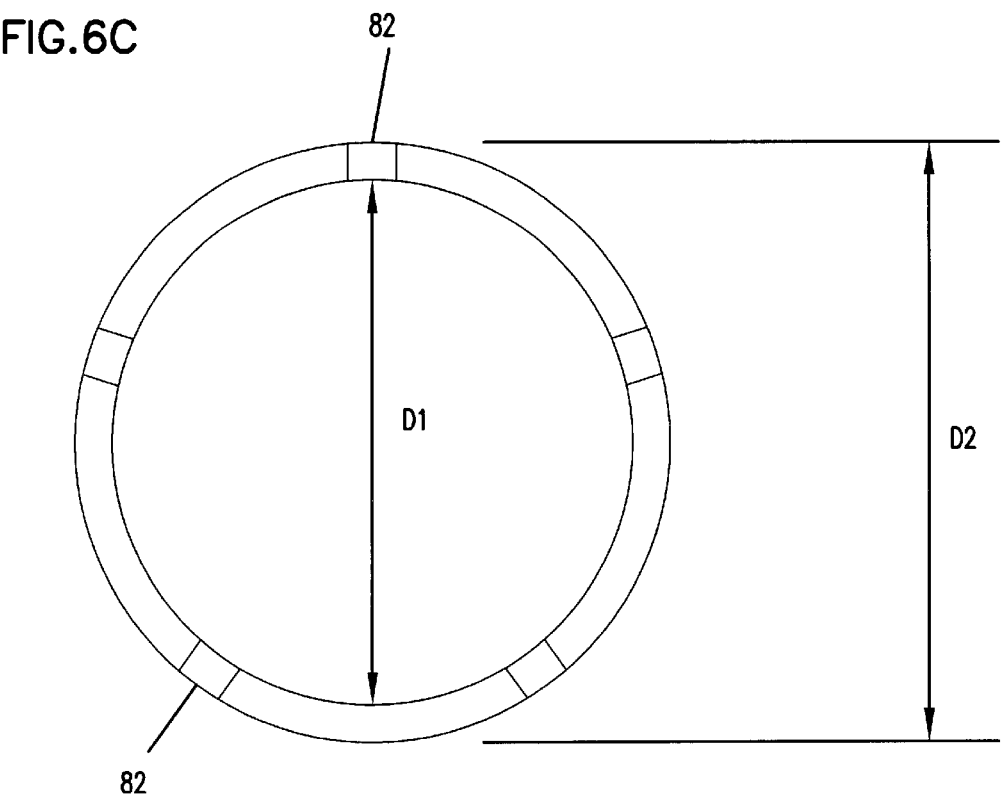
FIG. 6C is an end view of the stent of FIGS. 6A and 6B in its tubular configuration.
Figure 6A:
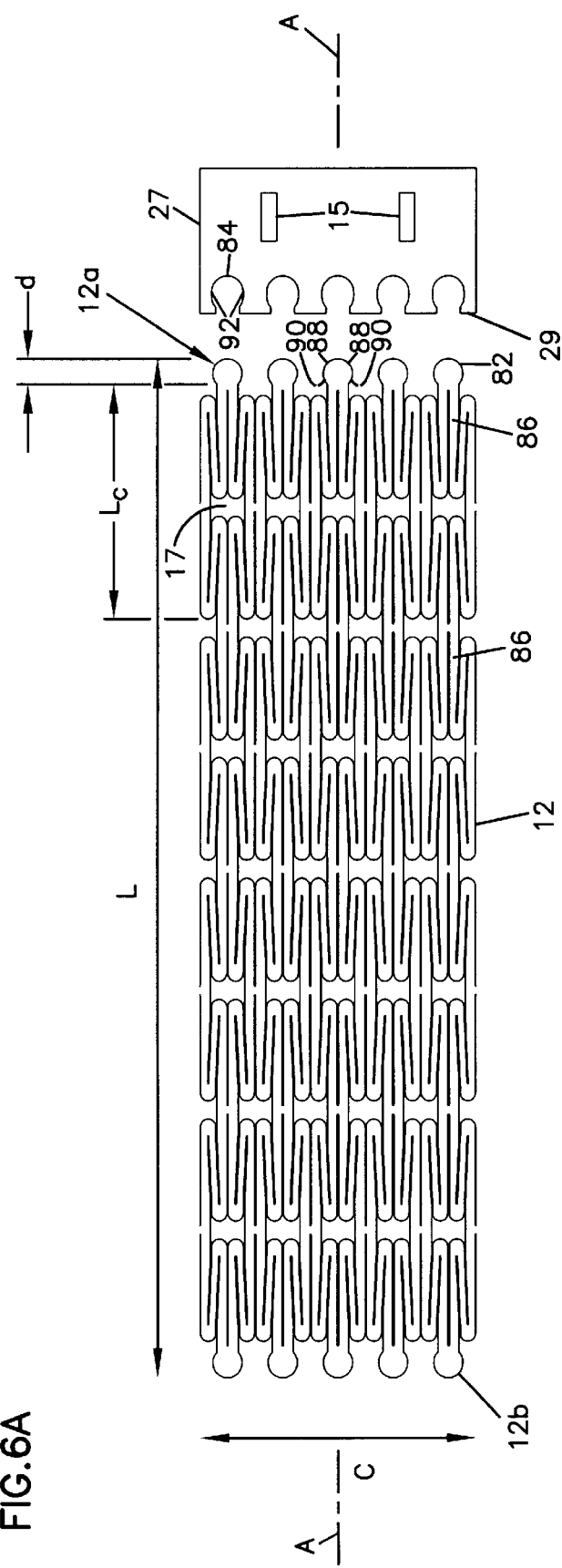
FIG. 6A is a plan view of a first stent having an interlock structure that interlocks with an interlock structure of a mating collar, the stent and the collar are shown cut longitudinally and laid flat with an axial separation between the stent proximal end and the mating collar.
Figure 6B:
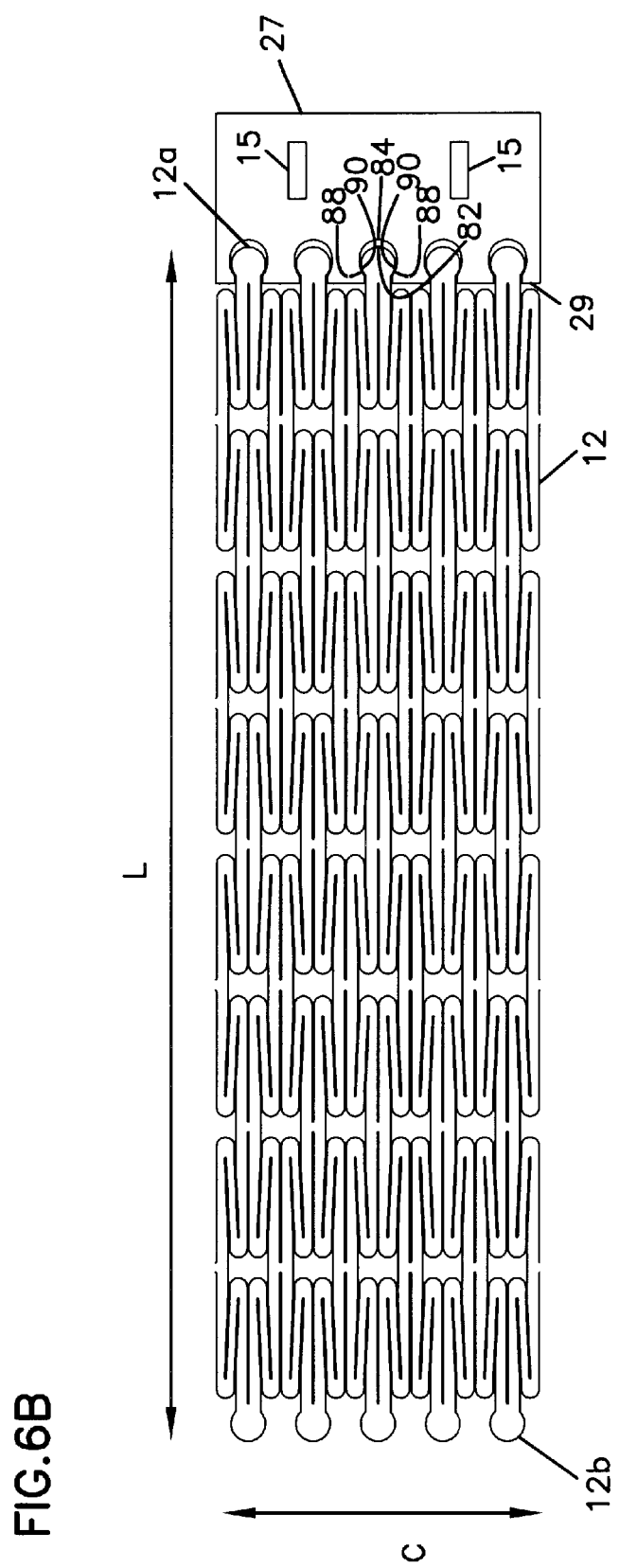
FIG. 6B is the view of FIG. 6A with the stent proximal end and mating collar shown interlocked.

FIGS. 6A and 6B illustrate the proximal end 12a of the stent 12 in relation to the marker 27 located at the proximal end of the attachment location 26. In FIGS. 6A and 6B, the stent 12 and the marker 27 have been cut longitudinally and laid flat. The stent 12 has a length L and a circumference C. In FIG. 6A, the marker 27 and the stent 12 are shown disengaged from one another. In FIG. 6B marker 27 and the stent 12 are shown interlocked.

Referring to FIG. 6A, the stent 12 includes a plurality of struts 86 (i.e., reinforcing members). A number of the plurality of struts, e.g. twelve, define a cell 17 (also shown in FIG. 2B). The stent 12 is made up of a plurality of interconnected cells 17. Still referring to FIG. 6A, each cell has a compressed or collapsed cell length Lc. At least some of the struts 86 of the cells 17 have free terminal ends that define the proximal and distal ends 12a and 12b of the stent 12. Male interlock structures 82 (i.e., keys) are provided at the free terminal ends of the struts 86. As shown in FIG. 6A, the male interlock structures 82 include enlargements in the form of circular projections that extend a distance d from the free terminal ends of the struts 86. In the preferred embodiment, the distance d that the male interlock structures 82 extend from the free terminal ends of the struts 86 is less than the collapsed cell length Lc of the cells 17. Thus, the male interlock structures 82 are within at most one collapsed cell length Lc of the cells 17.

The circular projections include interlock portions 88 that project outwardly from the struts 86 in a circumferential direction (i.e., in a direction coinciding with the circumference C of the stent 12). The interlock portions 88 include interlock surfaces 90 that face in an axial direction. The phrase "face in an axial direction" will be understood to mean that least a vector component of the surface 90 is perpendicular with respect to a longitudinal axis A—A of the stent 12. Thus, the surface 90 need not be completely perpendicular relative to the longitudinal axis of the stent 12 to be construed as facing in an axial direction. In other words, a surface aligned at oblique angle relative to the longitudinal axis of the stent 12 shall also be construed as facing in an axial direction since such surface has a vector component that is perpendicular relative to the longitudinal axis of the stent.

As best shown schematically in FIG. 6C, the male interlock structures 82 are preferably positioned within a region defined between an inner diameter D1 and an outer diameter D2 of the stent 12. Preferably, at least portions of the interlock surfaces 90 are located within 5 millimeters of the proximal end 12a of the stent 12. More preferably, at least portions of the interlock surfaces 90 are located within 3 millimeters of the proximal end 12a of the stent 12. Most preferably, at least portions of the interlock surfaces 90 are located within 2 millimeters of the proximal end 12a of the stent 12.

Still referring to FIGS. 6A and 6B, the marker 27 has an axial distal edge 29 facing the proximal end 12a of stent 12. Female interlock structures 84 (i.e., sockets, openings, keyways, etc.) are defined by the marker 27 adjacent the edge 29. The female interlock structures 84 are configured to have a complimentary mating geometry with respect to the male interlock structures 82 of the stent 12. For example, similar to the male interlock structures 82, the female interlock structures 84 are shown having generally rounded or circular shapes. Each of the female interlock structures 84 includes interlock surfaces 92 that face in an axial direction.

The geometry of the female interlock structures 84 is selected to mate with the predetermined geometry of the stent proximal end 12a such that the stent 12 and the marker 27 can be axially coupled or interlocked when the stent 12 is compressed at the mounting location 26. When the male and female interlock structures 82 and 84 are interlocked, the interlock surfaces 90 and 92 oppose and circumferentially overlap one another (see FIG. 6B) such that the stent is restricted from distal movement relative to the marker 27.

With the specific embodiment shown, the stent 12 and collar 27 are rotary coupled such that the stent 12 and collar 27 are restricted from relative rotary motion (i.e., about axis A—A) when the stent 12 is in the collapsed state. The predetermined stent geometry of the interlock structures 82 and the complementary mating geometry of the collar 27 do not restrict relative radial motion. Namely, as the self-expanding stent 12 expands radially, the male interlock structures 82 are free to radially move out of the female interlock structures 84. After such motion, the stent 12 is no longer coupled to the collar 27 and the stent 12 and collar 27 are free to move axially, radially or transversely to one another.

With the embodiment thus described, the mating features of the stent 12 and collar 27 prevent premature discharge of the stent 12 from a stent attachment location 26. As the outer sheath 16 is retracted, the sheath distal end 16b exposes the distal end 12b of the stent 12. At this point, the exposed distal end 12b of the stent 12 is free for limited expansion restrained by the remainder of the stent 12 being covered by the sheath 16 and by the attachment of the stent proximal end 12a to the proximal radiopaque marker 27.

Further retraction of the sheath 16, permits still further expansion of the stent 12. As the sheath distal end 12b approaches the stent proximal end 12a, the expansion of the stent material tends to urge the stent 12 to squeeze out of the small portion of the sheath 16 now covering the stent 12. However, this propensity is overcome by the attachment of the stent proximal end 12a to the collar 27 since any such ejection of the stent 12 would require axial separation of the stent 12 and collar 27. Such movement is prevented by the male interlock structures 82 and the female interlock structures 84.

Therefore, as long any portion of the sheath 16 overlies the male and female interlock structures 82 and 84, the proximal end 12a of the stent 12 cannot expand and cannot axially move away from the collar 27. Accordingly, the stent 12 is not released from the attachment location 26 until the physician has fully retracted the sheath 16 with the sheath distal end 16b retracted proximal to the proximal end of stent attachment location 26. The sheath distal end 16b is provided with a radiopaque marker 16b' (shown in FIGS. 2A and 2B) to permit visualization of the relative position of the sheath distal end 12b and the radiopaque markers 27, 28 of the stent attachment location 26.

With the structure and operation thus described, the physician has greater control of the release of the stent 12. More accurate stent positioning is attained. As long as even a small portion of the sheath 16 is not fully retracted (e.g., at least 1 mm extends distally to the proximal end 12a of the stent 12) the axial position of the stent 12 can be adjusted by advancing or retracting the inner tubular member 14. Also, as long as a small portion of the sheath 16 remains covered by the sheath 16 (e.g., at least 1 mm), the stent 12 can be readily re-sheathed by moving the sheath 16 in a distal direction.

In the embodiment of FIGS. 6A and 6B, the female and male interlock structures 82 and 84 have complementary mating geometries. It will be appreciated that in alternative embodiments, the female and male interlock structures need not have complementary/identical shapes. Instead, to provide an interlock, it is only necessary for a portion of the male interlock to be received in the female interlock such that mechanical interference or overlap between the interlocks prevents the interlocks from being axially separated. This can be accomplished without having identical mating shapes.

As described above, the interlock structure 84 of the inner tube 14 is provided on the proximal radiopaque marker 27. It will be appreciated that the interlock structure 84 need not be the same element as the radiopaque marker but could be a separate part. As a separate part, the interlock structure could be integrally formed/connected with the exterior of the inner tube 14, connected to the outer surface of the inner tube by conventional techniques (e.g., adhesive, fasteners, fusion bonding, etc.), or be connected to the outer surface of the inner tube 14 by one or more intermediate members. Further, the embodiment of FIGS. 6A and 6B shows that the interlock between the stent 12 and the tube 14 is provided at the proximal end 12*a* of the stent 12*b*. It will be appreciated that for certain embodiments, the interlock between the inner tube 14 and the stent 12 can be provided at the distal end 12*b* of the stent 12 (e.g., for a distally retractable sheath). Moreover, while the embodiment of FIGS. 6A and 6B shows interlock structures provided at all of the proximal ends of the struts 86, the invention is not so limited. For example, in some embodiments, only some of the struts 86 may include interlock structures. While in certain embodiments it may be desirable to use only one interlock structure at the end of the stent 12, it is preferable to use at least two separate/discrete interlock structures uniformly spaced about the circumference of the stent. It is more preferable to use at least 4 separate/discrete interlock structures that are preferably uniformly spaced about the circumference of the stent.

Figure 7:
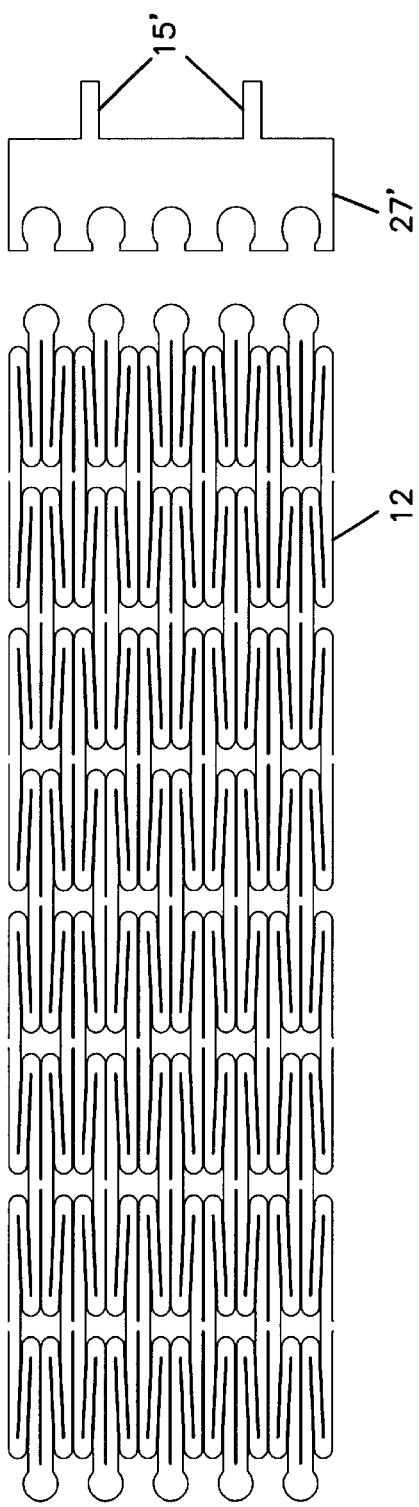
FIG. 7 is a laid flat, plan view of a second stent having an interlock structure that interlocks with an interlock structure of a mating collar, the collar includes rotational positioning indicators.
Figure 8:
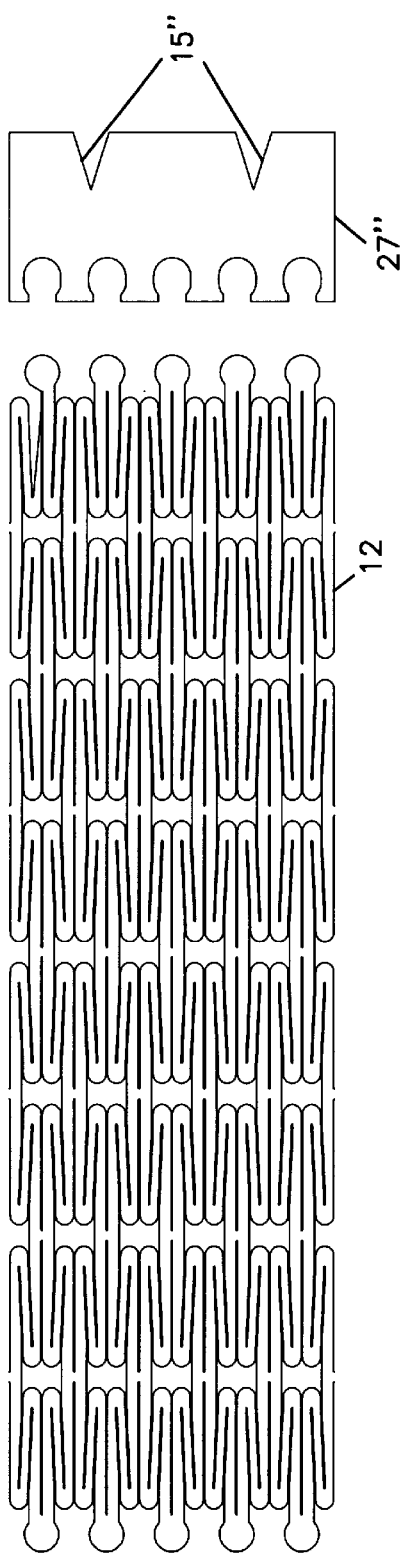
FIG. 8 is a laid flat, plan view of a third stent having an interlock structure that interlocks with an interlock structure of a mating collar, the collar includes rotational positioning notches.

The collar 27 may be provided with indicia to indicate to a physician the position of the collar 27 (and hence the stent 12) when the combination is in a patient's vessel and is being visualized under fluoroscopy. In the embodiment of FIGS. 6A and 6B, the indicia is shown as cutouts 15 in the collar 27. FIG. 7 shows a collar 27' having indicia in the form of proximal projections 15' off of the proximal edge of the collar 27'. FIG. 8 shows a collar 27" having indicia in the form of triangular notches 15" defined at the proximal edge of the collar 27". In the embodiments shown, the indicia 15, 15' and 15" are spaced apart circumferentially on their respective collars 27, 27' and 27" so that the indicia are 180 degrees apart.

In the embodiment of FIGS. 6A and 6B, the pattern and shape of the male interlock structures 82 and the female interlock structures 84 are symmetrical about the stent axis A—A. As a result, the stent 12 can be affixed to the collar 27 in any one of a plurality of rotary alignments about axis A—A.

Figure 9:
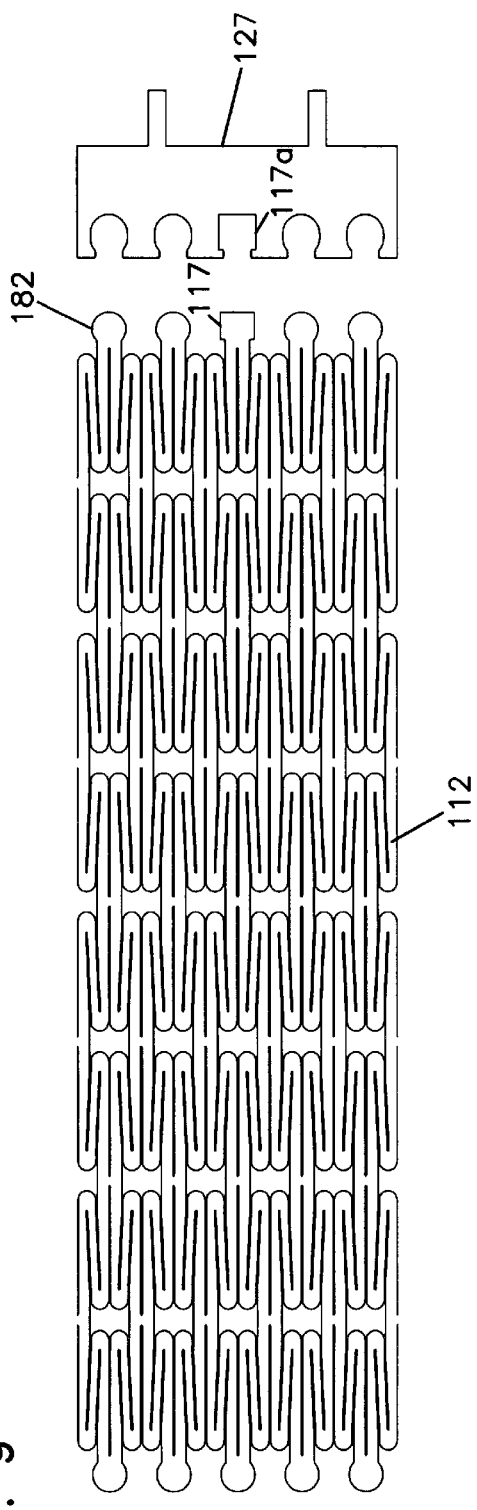
FIG. 9 is a laid flat, plan view of a fourth stent having an interlock structure that interlocks with an interlock structure of a mating collar, the stent and the collar include a rotational alignment key and keyway.

FIG. 9 illustrates an embodiment of a collar 127 and stent 112 where the symmetrical pattern is interrupted. In the example of FIG. 9, a single unique key 117 is provided (which, in the example shown, has a square geometry compared to the circular geometry of remaining male interlock structures 182). Similarly, the collar 127 has a unique keyway 117*a* to mate with the unique key 117. As a result, the stent 112 can only be affixed to the collar 127 in one rotary alignment.

In all of the above embodiments, once the position of a stent is fixed to a collar, a non-symmetrical stent feature (e.g., an opening for placement at a bifurcation in a vessel) can be aligned with the indicia (or, if desired, a single indicia can be provided on the collar). Therefore, a physician can easily visualize the position of any non-symmetrical stent feature.

Figure 10:
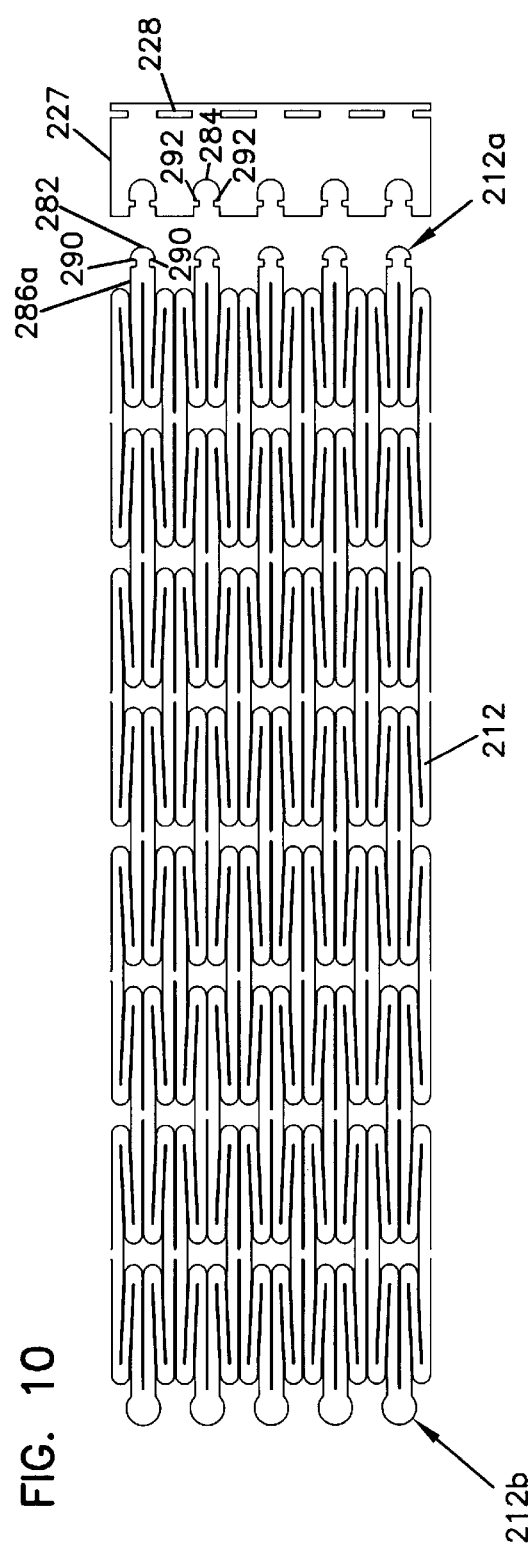
FIG. 10 is a laid flat, plan view of a fifth stent having an interlock structure that interlocks with an interlock structure of a mating collar.

FIG. 10 illustrates an embodiment of a stent 212 and radio-opaque collar 227 having another interlock configuration. The collar 227 has circumfential slots 228 for assisting in adhesively bonding the collar 227 to the outer surface of the inner tube 14. The stent 212 has proximal and distal ends 212*a* and 212*b*. The stent also includes proximal end struts 286*a* having free ends at which male interlock structures 282 are formed. The male interlock structures 282 are formed by notches cut into the proximal end struts 286*a*. The male interlock structures 282 include axially facing interlock surfaces 290 that face in a distal direction. Preferably, the surfaces 290 are located within 5 millimeters of the proximal end 212*a* of the stent 212.

The collar 227 includes female interlock structures 284 in the form of sockets. The sockets are partially defined by projections adapted to fit within the notches cut into the proximal end struts 286*a*. The projections define axially facing interlock surfaces 292 that face in a proximal direction. When the male and female interlock structures 282 and 284 are interlocked, the surfaces 290 and 292 oppose one another to prevent the male interlock structures 282 from being axially withdrawn from the female interlock structures 284.

FIG. 11 illustrates an embodiment of a stent 312 and radio-opaque collar 327 having another interlock configuration. The collar 327 has circumfential slots 328 for assisting in adhesively bonding the collar 327 to the outer surface of the inner tube 14. The stent 312 has proximal and distal ends 312*a* and 312*b*. The stent also includes proximal end struts 386*a* having free ends at which male interlock structures 382 are formed. The male interlock structures 382 are formed by enlarged heads (i.e., protuberances or keys) located at the ends of the end struts 386*a*. The male interlock structures 382 include axially facing interlock surfaces 390 that face in a distal direction. Preferably, the surfaces 390 are located within 5 millimeters of the proximal end 312*a* of the stent 312. The collar 327 includes female interlock structures 384 in the form of sockets. The female interlock structures 384 include axially facing interlock surfaces 392 that face in a proximal direction. When the male and female interlock structures 382 and 384 are interlocked, the surfaces 390 and 392 oppose one another to prevent the male interlock structures 382 from being axially withdrawn from the female interlock structures 384.

FIG. 12 illustrates an embodiment of a stent 412 including female interlock structures 484. The female interlock structures 484 preferably include distally facing interlock surfaces 492 located within 5 mm of a proximal end 412*a* of the stent 412. The female interlock structures 484 are sized to receive male interlock structures 482 in the form of rectangular posts. Preferably, the posts are connected to the outer surface of the inner tube 14 (e.g., integrally or otherwise). The posts define proximally facing interlock surfaces 490. When the female and male interlock structures 484 and 482 are coupled, the surfaces 490 and 492 engage each other to prevent distal movement of the stent 412 relative to the posts.

Figure 13:
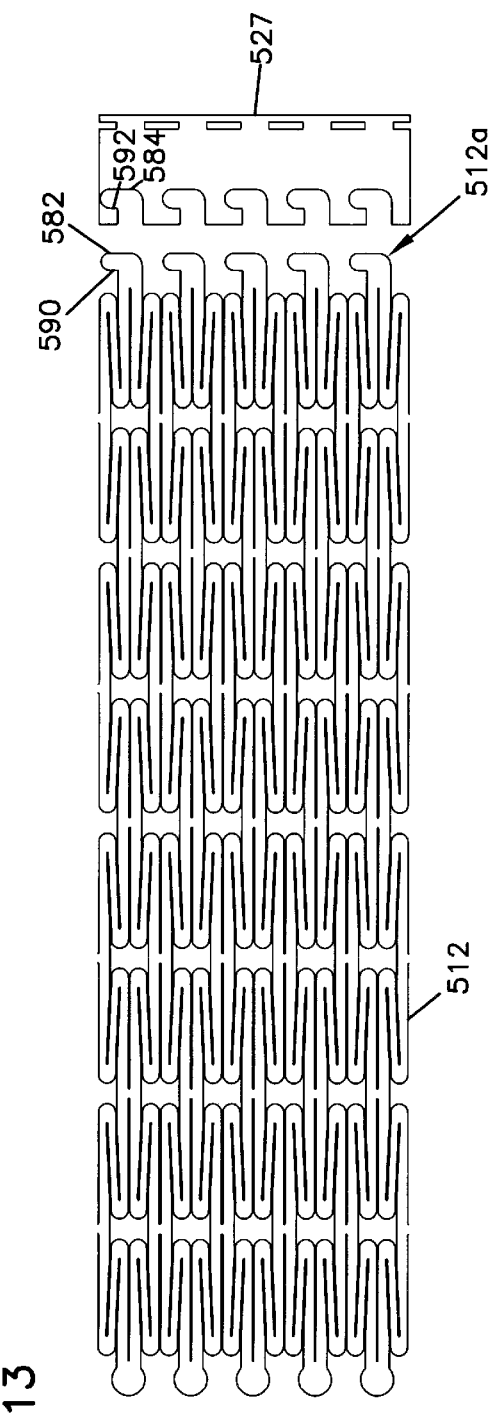
FIG. 13 is a laid flat, plan view of a eighth stent having an interlock structure that interlocks with an interlock structure of a mating collar.

FIG. 13 illustrates an embodiment of a stent 512 including male interlock structures 582 in the form of hooks. The male interlock structures 582 preferably include distally facing interlock surfaces 590 located within 5 mm of a proximal end 512*a* of the stent 512. The male interlock structures 582 are sized to fit within female interlock structures 584 defined by a collar 527. The female interlock structures 584 define proximally facing interlock surfaces 592. When the female and male interlock structures 584 and 582 are coupled, the surfaces 590 and 592 engage each other to prevent distal movement of the stent 512 relative to the collar 527.

Figure 14A:
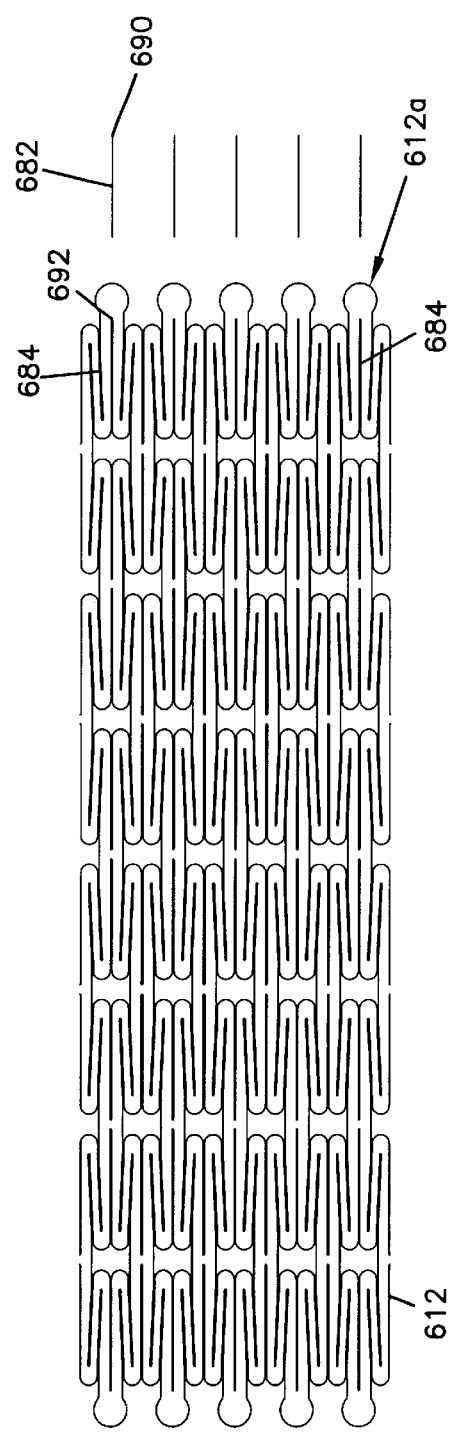
FIG. 14A is a laid flat, plan view of a ninth stent having an interlock structure that interlocks with outwardly projecting line-like projections formed on the inner body of a catheter.
Figure 14B:
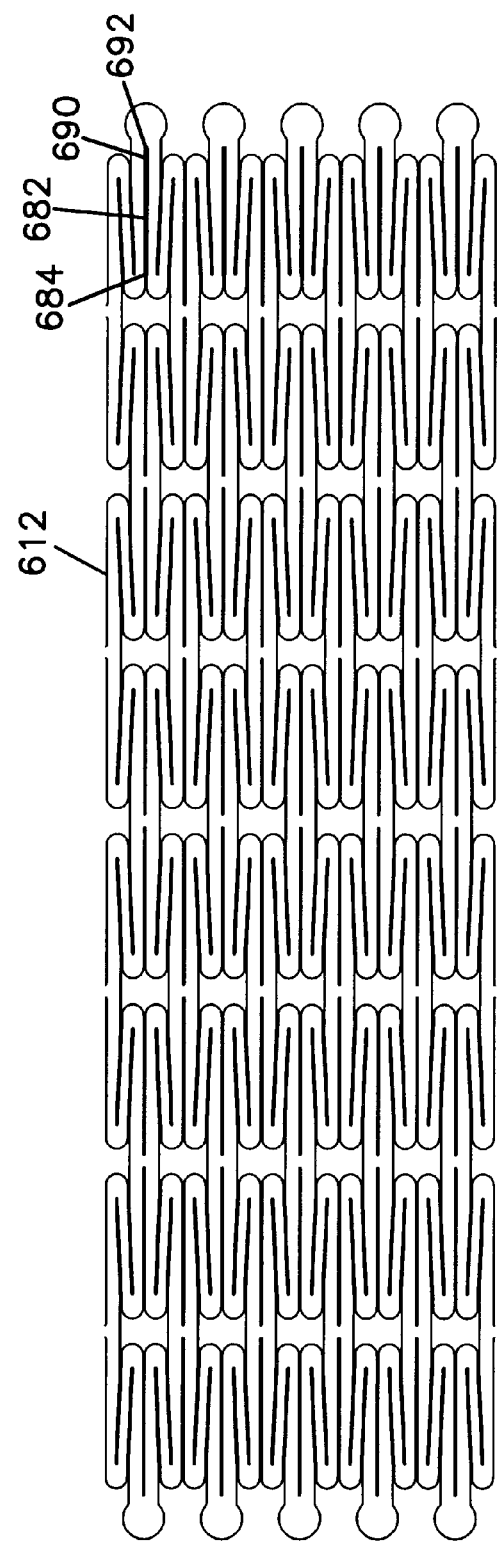
FIG. 14B shows the stent of FIG. 14A interlocked with the line-like projections.

FIGS. 14A and 14B illustrate an embodiment of a stent 612 including female interlock structures 684 in the form of longitudinal slots between or within struts. The female interlock structures 684 preferably include distally facing interlock surfaces 692 (e.g., defined by the proximal ends of the slots) located within 5 mm of a proximal end 612a of the stent 612. The female interlock structures 684 are sized to receive male interlock structures 682 in the form of linear posts. Preferably, the posts are connected to the outer surface of the inner tube 14 (e.g., integrally or otherwise). The posts define proximally facing interlock surfaces 690 (e.g., at the proximal ends of the posts). When the female and male interlock structures 684 and 682 are coupled as shown in FIG. 14B, the surfaces 690 and 692 engage each other to prevent distal movement of the stent 612 relative to the posts.

FIGS. 15A and 15B illustrate an embodiment of a stent 712 including female interlock structures 784 in the form of circular openings defined through enlarged strut ends of the stent 712. The female interlock structures 784 preferably include distally facing interlock surfaces 792 located within 5 mm of a proximal end 712a of the stent 712. The female interlock structures 784 are sized to receive male interlock structures 782 in the form of cylindrical posts or pins. Preferably, the posts are connected to the outer surface of the inner tube 14 (e.g., integrally or otherwise). The posts define proximally facing interlock surfaces 790. When the female and male interlock structures 784 and 782 are coupled as shown in FIG. 15B, the surfaces 790 and 792 engage each other to prevent distal movement of the stent 712 relative to the posts.

While the various embodiments of the present invention have related to stents and stent delivery systems, the scope of the present invention is not so limited. For example, while particularly suited for stent delivery systems, it will be appreciated that the various aspects of the present invention are also applicable to systems for delivering other types of self-expandable implants. By way of non-limiting example, other types of self-expanding implants include anastomosis devices, blood filters, grafts, vena cava filters, percutaneous valves, or other devices. Also, while it is preferred for the interlocks of the present invention to be within 5 millimeters of an end of their corresponding implant to enhance deployment control, larger spacings could be used for certain applications.

It has been shown how the objects of the invention have been attained in a preferred manner. Modifications and equivalents of the disclosed concepts are intended to be included within the scope of the claims.

What is claimed is:

1. A stent delivery system for delivering a stent to a deployment site in a body lumen of a patient's body, said stent delivery system comprising:

an elongated, flexible, hollow outer tubular member having a distal end and a proximal end;

an elongated, flexible, inner tubular member having a distal end and a proximal end;

said outer tubular member sized to be passed through said body lumen with said distal end advanced to said deployment site and with said proximal end external to said body for manipulation by an operator;

said inner member sized to be received within said outer tubular member with said inner member and said outer tubular member axially slideable relative to one another between a transport position and a deploy position;

said inner tubular member having a stent attachment location at said distal end of said inner tubular member, said stent attachment location having a proximal end and a distal end, said stent attachment location covered by said outer tubular member when said inner and outer tubular members are in said transport position, said stent attachment location exposed when said inner and outer tubular members are in said deploy position, sliding relative motion between said inner member and said outer tubular member from said transport position to said deploy position exposing first said distal end of said stent attachment location, an intermediate portion of said stent attachment location and then said proximal end of said stent attachment location;

a stent carried at said stent attachment location with a distal and proximal ends of said stent at said distal and proximal ends, respectively, of said stent attachment location;

said proximal end of said stent including a stent geometry having at least one male interlock structure that interlocks with said inner member to restrict said stent from axial movement relative to said inner member until said distal end of said outer tubular member moves proximally to said proximal end of said stent attachment location as said inner and outer members move toward said deploy position; and wherein the stent includes cell defining structures that define cells having a cell length, and wherein the inner member interlocks with the stent at an interlock location external of the cells, the interlock location being positioned not more than one cell length away from the cells.

2. A stent delivery system according to claim 1 wherein said proximal end of said stent releasably secured to said inner member to be restricted from rotary movement relative thereto until said distal end of said outer tubular member moves proximally to said proximal end of said stent attachment location as said inner and outer members move toward said deploy position.

3. A stent delivery system according to claim 2 wherein said inner member at said proximal end of said stent attachment location has a complimentary mating geometry to that of said stent geometry to restrict relative rotary movement between said proximal end of said stent and said inner member at said proximal end of said stent attachment location while permitting unrestricted radial expansion of said proximal end of said stent at said proximal end of said stent attachment location after said distal member of said outer tubular member has moved to expose said proximal end of said stent attachment location.

4. A stent delivery system according to claim 2 wherein said stent geometry is asymmetrical for said proximal end of said stent to be mated to said proximal end of said stent attachment location in a predetermined rotary alignment.

5. A stent delivery system according to claim 2 wherein said stent geometry is symmetrical for said proximal end of said stent to be mated to said proximal end of said stent attachment location in any one of a plurality of rotary positions.

6. A stent delivery system according to claim 1 wherein said inner member at said proximal end of said stent attachment location has a complimentary mating geometry to that of said stent geometry to restrict relative axial movement between said proximal end of said stent and said inner member at said proximal end of said stent attachment location while permitting unrestricted radial expansion of said proximal end of said stent at said proximal end of said stent attachment location after said distal member of said outer tubular member has moved to expose said proximal end of said stent attachment location.

7. A stent delivery system according to claim 6 wherein said complimentary mating geometry is formed in a radiopaque material at said proximal end of said attachment location.

8. A stent delivery system according to claim 6 wherein said complimentary mating geometry is formed in a collar positioned said proximal end of said stent attachment location.

9. A stent delivery system according to claim 1 wherein said stent geometry is asymmetrical for said proximal end of said stent to be mated to said proximal end of said stent attachment location in a predetermined rotary alignment.

10. A stent delivery system according to claim 9 further comprising a radiopaque indicator indicating a rotary position of said stent.

11. A stent delivery system according to claim 9 wherein said proximal end of said stent attachment location includes a radiopaque indicator indicating a rotary position of said attachment location.

12. A stent delivery system according to claim 1 wherein said stent geometry is symmetrical for said proximal end of said stent to be mated to said proximal end of said stent attachment location in any one of a plurality of rotary positions.

13. A stent delivery system according to claim 1 wherein said distal end of said outer tubular member has a radiopaque marking.

14. A stent delivery system according to claim 1 wherein said inner tubular member is hollow to track over a guide wire.

15. An implant delivery system comprising:
a catheter including an elongated member having an implant mounting location;
an expandable implant mounted on the elongated member at the implant mounting location, the implant being expandable from a compressed orientation to an expanded orientation, the implant including first and second ends, and a male interlock structure;
a sheath mounted on the elongated member, the sheath being positionable in a transport position in which the sheath covers the implant mounted at the implant mounting location, the sheath also being positionable in a deploy position in which the implant is exposed;
a radio-opaque marker positioned adjacent the implant mounting location, the radio-opaque marker being made of a radio-opaque material and having a female interlock structure;
wherein the male interlock structure of the implant interlocks with the female interlock structure of the radio-opaque marker to constrain axial movement of the implant relative to the elongated member when the implant is at least partially within the sheath.

16. The implant delivery system of claim 15, wherein the implant comprises a stent.

17. The implant delivery system of claim 15, wherein at least a portion of the male interlock structure is positioned within 5 millimeters of the first end of the implant.

18. The implant delivery system of claim 15, wherein the first end of the implant is a proximal end of the implant.

19. The implant delivery system of claim 15, wherein the implant includes a plurality of male interlock structures having at least portions positioned within 5 millimeters of the first end, and wherein the radio-opaque marker includes a plurality of female interlock structures for interlocking with the male interlock structures.

20. The implant delivery system of claim 15, wherein the male interlock structure includes an enlargement positioned at the first end of the implant.

21. The implant delivery system of claim 20, wherein the implant includes a plurality of enlargements at the first end of the implant.

22. The implant delivery system of claim 20, wherein the male interlock structure includes a circumferential projection positioned at the first end of the implant.

23. The implant delivery system of claim 22, wherein the implant includes a plurality of the circumferential projections at the first end of the implant.

24. A stent delivery system comprising:
a catheter including an elongated body having a stent mounting location;
an expandable stent mounted on the elongated body at the stent mounting location, the stent being expandable from a compressed orientation to an expanded orientation, the stent including first and second ends;
a sheath mounted on the elongated body, the sheath being positionable in a transport position in which the sheath covers the stent mounted at the stent mounting location, the sheath also being positionable in a deploy position in which the stent is exposed;
the stent including a plurality of struts at least some of which have free ends defining the first end of the stent, the free ends being adjacent cell defining regions of the stent, the cell defining regions defining cells having a cell length, the stent also including at least two male interlock structures positioned not more than one cell length away from the cells; and
the elongated body including female interlock structures that receive the male interlock structures to constrain axial movement of the stent relative to the elongated body when the stent is at least partially within the sheath.

25. The stent delivery system of claim 24, wherein the elongated body includes a radio-opaque marker positioned adjacent to the stent mounting location, and wherein the marker defines the female interlock structures.

26. The stent delivery system of claim 24, wherein the first end of the stent is a proximal end of the stent.

27. The stent delivery system of claim 24, wherein the male interlock structures are rounded enlargements.

28. The stent delivery system of claim 24, wherein the male interlock structures are positioned exclusively between inner and outer diameters of the stent.

29. The stent delivery system of claim 24, wherein the male interlock structures are uniformly spaced about a circumference of the stent.

30. The stent delivery system of claim 24, wherein the stent includes at least four of the male interlock structures.

31. The stent delivery system of claim 24, wherein the male interlock structures are integral male interlock structures located at the free ends of the struts.

32. An implant delivery system comprising:
a catheter including an elongated member having an implant mounting location;
an expandable implant mounted on the elongated body at the implant mounting location, the implant being expandable from a compressed orientation to an expanded orientation, the implant including first and second ends;
a sheath mounted on the elongated member, the sheath being positionable in a transport position in which the sheath covers the implant mounted at the implant mounting location, the sheath also being positionable in a deploy position in which the implant is exposed;
the implant including a male interlock structure having an enlargement defining a circumferential projection positioned at the first end of the implant, and the elongated body including a female interlock structure adapted to receive the male interlock structure when the implant is in the compressed orientation, the male and female interlock structures interlocking to constrain axial movement of the implant relative to the elongated member when the implant is at least partially within the sheath;

at least a portion of the male interlock structure being positioned within 5 millimeters of the first end of the implant; and wherein the elongated body includes a radio-opaque marker positioned adjacent to the implant mounting location, and wherein the marker defines the female interlock structure.

33. The implant delivery system of claim 32, wherein the implant includes a plurality of the circumferential projections at the first end of the implant.

34. A stent delivery system comprising:

a catheter including an elongated member having a stent mounting location;

an expandable stent mounted on the elongated body at the stent mounting location, the stent being expandable from a compressed orientation to an expanded orientation, the stent including first and second ends;

a sheath mounted on the elongated body, the sheath being positionable in a transport position in which the sheath covers the stent mounted at the stent mounting location, the sheath also being positionable in a deploy position in which the stent is exposed;

the stent including a plurality of struts at least some of which have free ends defining the first end of the stent, the stent also including at least two male interlock structures having rounded enlargements, the male interlock structures being positioned at the free ends of the struts adjacent the first end of the stent, the free ends being adjacent cell defining regions of the stent; and the elongated body including female interlock structures that receive the male interlock structures to constrain axial movement of the stent relative to the elongated member when the stent is at least partially within the sheath.

35. A stent delivery system comprising:

a catheter including an elongated member having a stent mounting location;

an expandable stent mounted on the elongated member at the stent mounting location, the stent being expandable from a compressed orientation to an expanded orientation, the stent including a stent body having first and second ends;

a sheath mounted on the elongated member, the sheath being positionable in a transport position in which the sheath covers the stent mounted at the stent mounting location, the sheath also being positionable in a deploy position in which the stent is exposed;

the stent body having a cell defining region including a plurality of cells, each cell having a compressed cell length, one of the first and second ends of the stent body including at least one integral male interlock structure, the integral male interlock structure being located not more than one compressed cell length away from the cell defining region of the stent body; and the elongated member including female interlock structures that receive the male interlock structures to constrain axial movement of the stent relative to the elongated member when the stent is at least partially within the sheath.

36. The stent delivery system of claim 35 wherein the stent body defines an inner diameter and an outer diameter, the male interlock structure being located in a region defined between the inner diameter and the outer diameter.

37. The stent delivery system of claim 36 wherein the male interlock structure has a cross-sectional curvature about a longitudinal axis of the stent.

38. The stent delivery system of claim 35 wherein the stent body includes a plurality of integral male interlock structure.

39. A stent delivery system comprising:

a catheter including an elongated body having a stent mounting location;

an expandable stent mounted on the elongated body at the stent mounting location, the stent being expandable from an undeployed orientation to a deployed orientation, the stent including first and second ends and a cell defining region located between the first and second ends, the cell defining regions defining cells each having a cell length, the stent also including at least one or more male interlock structures positioned not more than one cell length away from the cell defining region; and the elongated body including at least one or more female interlock structures that receive the one or more male interlock structures to constrain axial movement of the stent relative to the elongated body.

40. The stent delivery system of claim 39, wherein the expandable stent includes at least two male interlock structures positioned not more than one cell length away from the cell defining region, and wherein the elongated body includes at least two female interlock structures that receive the at least two male interlock structures.

41. A stent delivery system comprising:

a catheter including an elongated member having a stent mounting location;

an expandable stent mounted on the elongated body at the stent mounting location, the stent being expandable from an undeployed orientation to a deployed orientation, the stent including first and second ends, the stent also including one or more male interlock structures each having a rounded enlargement, the one or more male interlock structures being positioned at the first end of the stent; and the elongated body including one or more female interlock structures that receive the one or more male interlock structures to contratin axial movement of the stent relative to the elongated member.

42. The stent delivery system of claim 41, wherein the expandable stent includes at least two male interlock structures each having a rounded enlargement, and wherein the elongated body includes at least two female interlock structures that receive the at least two male interlock structures.

* * * * *

UNITED STATES PATENT AND TRADEMARK OFFICE
CERTIFICATE OF CORRECTION

PATENT NO. : 6,623,518 B2
DATED : September 23, 2003
INVENTOR(S) : Thompson et al.

It is certified that error appears in the above-identified patent and that said Letters Patent is hereby corrected as shown below:

Column 12,
Lines 10-11, "location with a distal" should read -- location with distal --
Line 66, "said attachment" should read -- said stent attachment --

Column 16,
Line 15, "structure." should read -- structures. --
Line 54, "to contratin axial" should read -- to constrain axial --

Signed and Sealed this

Twenty-sixth Day of October, 2004

JON W. DUDAS
*Director of the United States Patent and Trademark Office*